United States Patent [19]

Takeshi

[11] Patent Number: 5,545,037
[45] Date of Patent: Aug. 13, 1996

[54] INTERARCH ORTHODONTIC COIL SPRING

[75] Inventor: Watanabe Takeshi, Ohkuma-machi, Japan

[73] Assignee: GAC International, Inc., Central Islip, N.Y.

[21] Appl. No.: 335,607

[22] Filed: Nov. 8, 1994

[51] Int. Cl.⁶ .................................................. A61C 3/00
[52] U.S. Cl. .................................................. 433/21; 433/19
[58] Field of Search ..................................... 433/21, 19, 5

[56] References Cited

U.S. PATENT DOCUMENTS

| | | | |
|---|---|---|---|
| 3,087,245 | 4/1963 | Asher | 433/5 |
| 3,618,214 | 11/1971 | Armstrong | 32/14 A |
| 3,691,635 | 9/1972 | Wallshein | 433/21 |
| 3,772,789 | 11/1973 | DeWeoskin | 32/14 D |
| 3,798,773 | 3/1974 | Northcutt | 32/14 E |
| 4,259,065 | 3/1981 | DeWoskin | 433/5 |
| 4,600,382 | 7/1986 | Foster | 433/5 |
| 4,708,646 | 11/1987 | Jasper | 433/19 |
| 4,795,342 | 1/1989 | Jones | 433/19 |
| 4,802,849 | 2/1989 | Collins, Jr. | 433/19 |
| 4,849,032 | 7/1989 | Kawaguchi | 148/11.5 |
| 5,046,948 | 9/1991 | Miura | 433/21 |
| 5,074,784 | 12/1991 | Sterrett et al. | 433/18 |
| 5,120,218 | 6/1992 | Hanson | 433/19 |

Primary Examiner—John J. Wilson
Attorney, Agent, or Firm—Kenyon & Kenyon

[57] ABSTRACT

An orthodontic coil spring assembly is provided for installment on orthodontic brackets bonded on a patient's teeth for applying interarch tension. The coil spring assembly includes a coil spring and two attachment plates. Each of the attachment plates includes a first end connected with one of the ends of the coil spring, and an opposite second end connectable with an orthodontic bracket. The distance between the first and second ends of each plate is about 6 mm. Each plate also includes a narrowed neck portion between the first and second ends to facilitate deformation of the plate during installation on the brackets. An expandable sheath may be provided for covering the coil spring to inhibit pinching of the patient's cheeks by the coil spring.

33 Claims, 3 Drawing Sheets

INTERARCH ORTHODONTIC COIL SPRING

FIELD OF THE INVENTION

The present invention relates generally to orthodontic appliances and, more particularly, to interarch orthodontic coil springs provided for applying corrective forces to teeth.

BACKGROUND INFORMATION

Interarch orthodontic coil springs are used for applying interarch tension during orthodontic treatment. The coil spring is typically attached at one end to a bracket bonded to a tooth on a patient's upper jaw and at the opposite end to a bracket bonded to a tooth on the lower jaw. Interarch tension may be applied to achieve a variety of objectives including stimulating growth, inducing incisor advancement, uprighting mandibular molars, and retracting the anterior segment of the maxillary arch.

One of the problems of some prior coil spring designs is that when attached to a bracket, the coil spring is caused to be bent over the buccal surface of the bracket. Such bending of the coil spring may reduce its effectiveness and shorten its useful life.

In addition, if the coil spring is positioned over the buccal surface of the bracket, the spring may more readily engage and irritate the patient's inner cheeks. Such irritation may cause some patients to remove or break these coil springs.

Moreover, if the coil spring is located over the buccal surface of the bracket, it may more readily engage or interfere with an arch wire retained in the bracket. Such interference or engagement between the arch wire and the coil spring may restrict movement of the arch wire and thereby lengthen the period of orthodontic treatment.

One object of the present invention is to provide a coil spring assembly that can be installed on orthodontic brackets without substantial bending of the coil spring. Another object of the invention is to provide a coil spring assembly that can be installed on orthodontic brackets while substantially limiting placement of the coil spring over the buccal surface of the brackets and limiting contact between the coil spring and arch wires retained in the brackets.

SUMMARY OF THE INVENTION

An orthodontic coil spring assembly is provided for installment on orthodontic brackets bonded on a patient's teeth for applying interarch tension. The coil spring assembly includes a coil spring and two attachment plates. Each of the attachment plates includes a first end connected with one of the ends of the coil spring, and an opposite second end connectable with an orthodontic bracket. The distance between the first and second ends of each plate is about 6 mm. Each plate also includes a narrowed neck portion between the first and second ends to facilitate deformation of the plate during installation on the brackets.

The coil spring assembly in accordance with the invention can be installed on orthodontic brackets such that the coil spring is not substantially bent after installation. In addition, the coil spring assembly can be installed on orthodontic brackets while substantially limiting placement of the coil spring over the buccal surface of the brackets and limiting contact between the coil spring and arch wires retained in the brackets.

An expandable sheath may be provided for covering the coil spring to inhibit pinching of the patient's cheeks by the coil spring.

Other advantages of the orthodontic coil spring assembly of the present invention will become apparent in view of the following detailed description and accompanying drawings.

DETAILED DESCRIPTION

Figure 1:
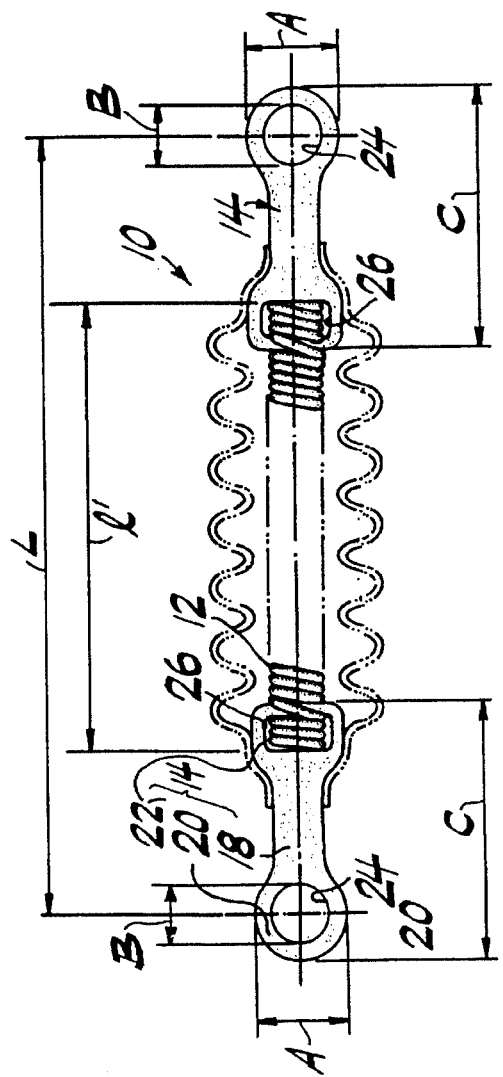
FIG. 1 is a front view of an interarch orthodontic coil spring assembly in accordance with one embodiment of the present invention.
Figure 2:
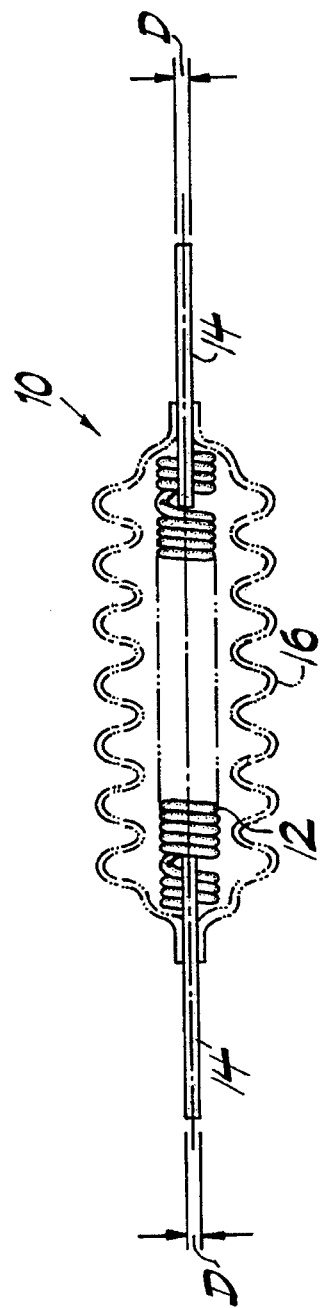
FIG. 2 is a side view of the coil spring assembly shown in FIG. 1.

FIGS. 1 and 2 illustrate front and side views, respectively, of a coil spring assembly 10 in accordance with one embodiment of the invention. The coil spring assembly 10 comprises an orthodontic coil spring 12 and a pair of attachment plates 14, each connected to an opposite end of the coil spring 12. A flexible cover or sheath 16 may be provided to cover the coil spring.

The attachment plates 14 each comprise an elongated central neck member 18 connected at one end thereof to an enlarged ring-shaped portion 20 and at an opposite end to an enlarged generally rectangular-shaped portion 22. The ring-shaped portion 20 includes a circular hole 24 extending therethrough to facilitate attachment of the plate to an orthodontic bracket. The rectangular-shaped portion 22 includes a generally rectangular-shaped hole 26 extending therethrough. The ring-shaped portion 20 and the rectangular-shaped portion 22 are integrally formed with a neck portion 18 therebetween.

As shown in FIG. 1, the outer diameter of the ring portion 20 is indicated by reference character A, and the diameter of the hole 24 therein is indicated by reference character B. The overall length of the plate 10 is indicated by reference character C, and the thickness of the plate is indicated by reference character D (FIG. 2). The following dimensions for the plate have been found to be particularly suitable:

A: 2.2 mm
B: 1.4 mm

C: 6.0 mm

D: 0.3 mm

The neck portion 18 of the plate 14 is narrowed relative to the end portions 20, 22 to allow a practitioner to readily deform the plate for proper mounting on an orthodontic bracket. The plate 14 can be bent and/or twisted in the region of the neck portion as will be described.

The plate 14 may be formed from a variety of materials suitable for use in an oral environment including stainless steel and plastics. If the plate comprises a metal, it may be softened through heat treatment to further facilitate deformation thereof during installment.

The orthodontic coil spring 12, which may have a spring force of 150 g, can be formed from a nickel-titanium alloy wire or other suitable wires. It is secured to the plates 14 by inserting a few coils at the ends of the spring partly into the rectangular holes 26 at the ends of the plates 14. Thereafter, the ends of the coil spring 12 are laser welded or otherwise fixed to the plates 14 to secure the parts together.

The length of the coil spring 12 should be selected such that when it is in place in the patient's mouth, it is slightly extended or stretched when the mouth is closed. (As shown in FIGS. 1 and 2, the coil spring 12 is in a closed position, that is, it is substantially unstretched prior to installment.) The coil spring 12 thus can exert corrective orthodontic forces even when the patient's teeth are in occlusion, as may be the case particularly when the patient is asleep.

The length of the coil spring 12 is preferred to be sufficiently long such that when the patient's mouth is open while the patient is, for example, talking or eating, the expanded coil spring does not exceed twice its original unstretched length. Coil springs stretched continuously beyond twice their unstretched lengths have been found to be prone to premature breakage. This type of failure is typically caused by microscopic imperfections in the springs that would otherwise not cause the springs to break unless they are continuously overstretched. It has been found that selecting the size of the coil spring in accordance with these criteria allows effective application of forces on the teeth and lengthens the useful life of the spring.

The following combinations of lengths for the coil spring (indicated by l' in FIG. 1) and the coil spring assembly (defined by the distance between ring hole 24 centers designated by L) have been found to be suitable for commercial applications:

| L | l' |
|---|---|
| 18 mm | 9 mm |
| 23 mm | 14 mm |
| 28 mm | 19 mm |

The sheath 16 may be formed from a silicone material. The sheath 16 is designed to have a bellows-type configuration such that it can expand and contract to correspond to the state of the coil spring and to thus cover the coil spring when in use. The coils of the coil spring are thus prevented from pinching the inner cheeks of the patient. It has been found that cheek irritation resulting from coil spring pinching causes some patients, particularly children, to remove or break the springs.

Figure 3:
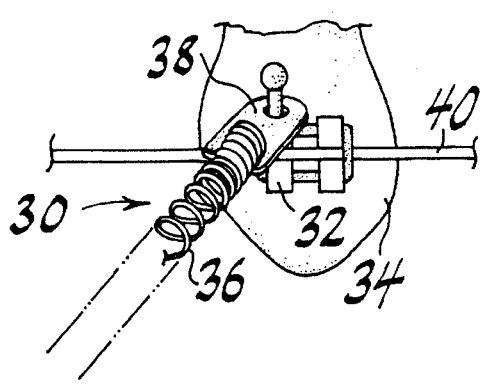
FIG. 3 is a perspective view of a portion of a prior art interarch orthodontic coil spring assembly shown mounted on an orthodontic bracket affixed to a tooth.
Figure 4:
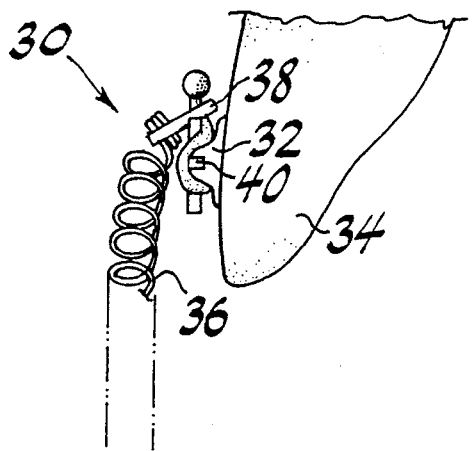
FIG. 4 is a side view of the mounting of the prior art coil spring assembly shown in FIG. 3.

FIGS. 3 and 4 illustrate one end of a prior art coil spring assembly 30 mounted on a bracket 32 bonded to a tooth 34. The prior art coil spring assembly 30 comprises a coil spring 36 attached to an attachment plate 38. The attachment plate 38 has a substantially smaller length than the previously described plate 14 of FIGS. 1 and 2. In addition, the plate 38 is not easily deformable due to its small size. As a result of this plate design, the coil spring 36 is caused to be bent proximate its connection to the plate 38 when installed on the bracket 32 as shown particularly in FIG. 4. The coil spring 36 is also caused to be positioned over the buccal surface of the bracket 32 such that it potentially engages or interferes with an arch wire 40 secured to the bracket 32. Such interference or engagement between the arch wire 40 and the coil spring 36 may restrict movement of the arch wire 40 and thereby lengthen the period of orthodontic treatment.

Moreover, if the coil spring 36 is positioned over the buccal surface of the bracket 32, the spring may irritate the patient's inner cheeks. Such irritation may cause some patients to remove or break the coil spring.

Figure 5:
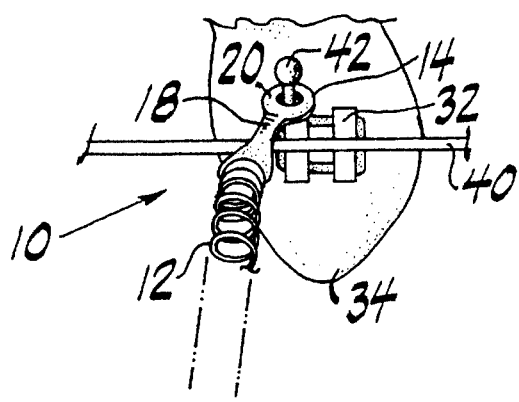
FIG. 5 is a perspective view of a portion of a coil spring assembly in accordance with the invention shown mounted on an orthodontic bracket affixed to a tooth.
Figure 6:
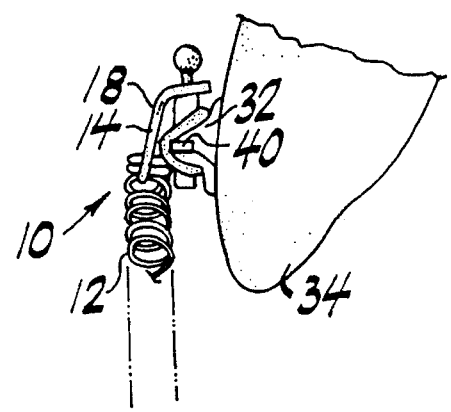
FIG. 6 is a side view of the mounting of the coil spring assembly shown in FIG. 5.

FIGS. 5 and 6 illustrate the application of the coil spring assembly 10 in accordance with the invention. As shown in the drawings, the ring portion 20 of the plate 14 is placed over a vertical post 42 extending from the bracket 32. The plate 14 has been deformed in the neck portion 18 thereof to extend substantially over the buccal surface of the bracket 32. As a result, the coil spring 12 is generally not bent about the buccal surface of the bracket 32 and extends substantially along a straight line from the plate 14 when installed unlike the prior coil spring assembly 30 of FIGS. 3 and 4.

The plate 14 is sized such that the coil spring 12 is also spaced away from the arch wire 40 to avoid interference therewith. As previously noted, the preferred overall length of the plate is about 6 mm. This length has been found to provide suitable protection from coil-arch wire interference when used with commercially available brackets.

FIGS. 7–11 each illustrate coil spring assemblies in accordance with other embodiments of the invention. The plate design in each embodiment is varied for use on particular teeth or to suit particular practitioner preferences or techniques.

Figure 7:
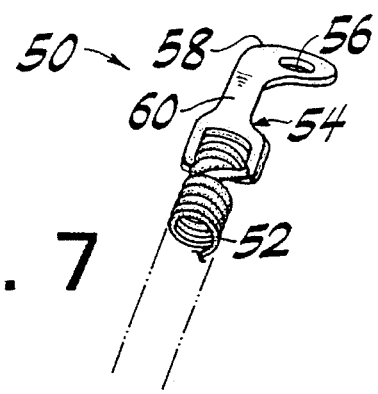
FIG. 7 is a perspective view of a portion of a coil spring assembly in accordance with another embodiment of the invention.

FIG. 7 illustrates a portion of a coil spring assembly 50 comprising a coil spring 52 and a plate 54 attached to one end of the spring. The plate 54 differs from the plate 14 of FIGS. 1 and 2 in that the center of the hole 56 in the ring portion 58 of the plate 54 is offset from the longitudinal axis of the neck portion 60 of the plate.

Figure 8:
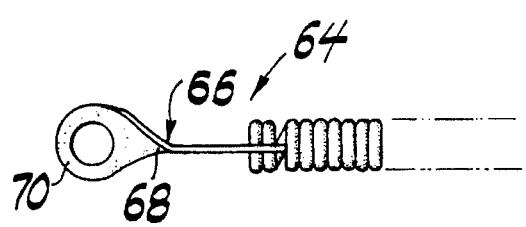
FIG. 8 is a side view of a portion of a coil spring assembly in accordance with another embodiment of the invention.

The coil spring assembly 64 of FIG. 8 comprises a plate 66, the neck portion 68 of which is twisted approximately 90° about its longitudinal axis. The ring portion 70 of the plate 66 is, as a result, substantially perpendicular to the rest of the plate.

Figure 9:
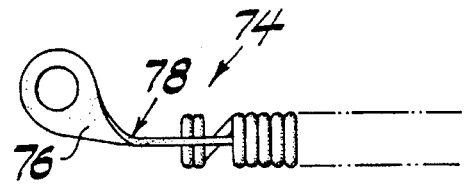
FIG. 9 is a side view of a portion of a coil spring assembly in accordance with another embodiment of the invention.

The coil spring assembly 74 of FIG. 9 includes a plate 76 similar to the plate 66 shown in FIG. 8. The plate 76 of FIG. 9 is bent generally about an axis perpendicular to the longitudinal axis of the neck portion 78 of the plate 76.

Figure 10:
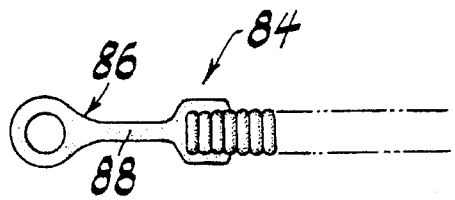
FIG. 10 is a front view of a portion of a coil spring assembly in accordance with another embodiment of the invention.

FIG. 10 illustrates a coil spring assembly 84 that includes a plate 86, the neck portion 88 of which is narrower in width relative to the rest of the plate than the neck portion 18 of the plate 14 of FIGS. 1 and 2. A narrower neck portion is provided to further facilitate deformation of the plate 86 during installment on a bracket.

Figure 11:
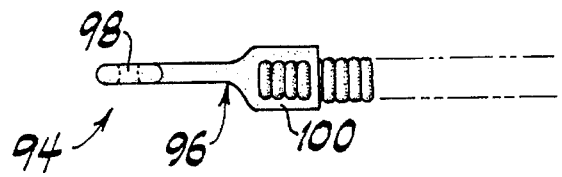
FIG. 11 is a front view of a portion of a coil spring assembly in accordance with another embodiment of the invention.

The coil spring assembly 94 shown in FIG. 11 includes a plate 96 that is similar to the plate 86 of FIG. 10. The ring portion 98 of the plate 96 is however oriented on a plane substantially perpendicular to the plane of the rectangular end portion 100.

The present invention has been described in the foregoing specification with respect to specific embodiments that serve as examples to illustrate the invention rather than to limit its scope. Modifications may be made thereto without departing from the broader teachings of the invention.

I claim:

1. An interarch orthodontic coil spring assembly for use with an orthodontic bracket adapted to support an orthodontic arch wire, said coil spring assembly comprising:
    a coil spring having opposite ends; and
    a deformable attachment plate attached to each end of said coil spring, each of said plates having a first end secured to one end of said coil spring and an opposite second end connectable with an orthodontic bracket,
    each of said deformable attachment plates including an elongated neck portion between said first and second ends, said neck portion having smaller exterior dimensions than said first and second ends to facilitate deformation of said plate, and
    wherein the distance between the first and second ends of each plate is sufficiently long to limit contact between the coil spring and the arch wire when the coil spring assembly has been installed on said bracket.

2. The orthodontic coil spring assembly of claim 1, wherein said distance is about 6 mm.

3. The orthodontic coil spring assembly of claim 1, further comprising an expandable sheath positioned around said coil spring to limit contact between said coil spring and a patient.

4. The orthodontic coil spring assembly of claim 3, wherein said sheath comprises silicone material.

5. The orthodontic coil spring assembly of claim 3, wherein said sheath has a bellowed configuration.

6. The orthodontic coil spring assembly of claim 1, wherein said second end of each plate includes a hole extending therethrough to facilitate connection with the orthodontic bracket.

7. The orthodontic coil spring assembly of claim 6, wherein said hole is circular and has a diameter of about 1.4 mm.

8. The orthodontic coil spring assembly of claim 1, wherein each plate is bendable and twistable for proper installation of said coil spring assembly.

9. The orthodontic coil spring assembly of claim 1, wherein each plate includes a hole extending therethrough at said first end adapted for receiving at least one coil of said coil spring for securing said plate to said coil spring.

10. The orthodontic coil spring assembly of claim 1, wherein said first end of each plate is laser welded to one end of said coil spring.

11. The orthodontic coil spring assembly of claim 1, wherein said second ends of said attachment plates each include a hole extending therethrough connectable with respective orthodontic brackets.

12. The orthodontic coil spring assembly of claim 11, wherein the distance between the geometric centers of said holes is about 18 mm.

13. The orthodontic coil spring assembly of claim 11, wherein the distance between the geometric centers of said holes is about 23 mm.

14. The orthodontic coil spring assembly of claim 11, wherein the distance between the geometric centers of said holes is about 28 mm.

15. The orthodontic coil spring assembly of claim 11, wherein said elongated neck portion of each plate includes a longitudinal axis therethrough and wherein the geometric center of said hole in said second end of each plate is offset from said longitudinal axis.

16. The orthodontic coil spring assembly of claim 1, wherein said neck portion is bent at an axis substantially perpendicular to the longitudinal axis of said neck portion.

17. The orthodontic coil spring assembly of claim 1, wherein in each plate, the first end is oriented in a plane substantially perpendicular to a plane on which the second end is oriented.

18. The orthodontic coil spring assembly of claim 1, wherein said second end of each plate has a generally rounded outer shape.

19. The orthodontic coil spring assembly of claim 1, wherein each plate has a thickness of about 0.3 mm.

20. The orthodontic coil spring assembly of claim 1, wherein each attachment plate comprises a softened heat-treated metal.

21. A formable attachment plate for attachment to an orthodontic coil spring, said attachment plate comprising a first end connectable with one end of the coil spring and an opposite second end connectable with an orthodontic bracket, wherein the distance between the first and second ends of said plate is about 6 mm, said plate also including a deformable narrowed neck portion between said first and second ends to facilitate deformation of the plate during installation on the bracket.

22. The attachment plate of claim 21, wherein said second end of said plate includes a hole extending therethrough to facilitate connection with the orthodontic bracket.

23. The attachment plate of claim 22, wherein said hole is circular and has a diameter of about 1.4 mm.

24. The attachment plate of claim 22, wherein said neck portion has a longitudinal axis therethrough and wherein the geometric center of said hole in said second end is offset from said longitudinal axis.

25. The attachment plate of claim 21, wherein said neck portion is bendable and twistable.

26. The attachment plate of claim 21, further comprising a hole extending therethrough at said first end adapted for receiving at least one coil of said coil spring for securing said plate to said coil spring.

27. The attachment plate of claim 21, wherein said neck portion is elongated and includes a longitudinal axis therethrough, and wherein said neck portion is bendable along an axis substantially perpendicular to said longitudinal axis.

28. The attachment plate of claim 21, wherein the first end and the second end are each oriented in a plane substantially perpendicular to that of the other.

29. The attachment plate of claim 21, wherein said second end has a generally rounded outer shape.

30. The attachment plate of claim 21, wherein said plate has a thickness of about 0.3 mm.

31. The attachment plate of claim 21, wherein said plate comprises a softened heat-treated metal.

32. An interarch orthodontic coil spring assembly, comprising:
    a coil spring having opposite ends; and
    two formable attachment plates, each including a first end connected with a different one of said ends of said coil spring, and an opposite second end connectable with an orthodontic bracket, wherein the distance between the first and second ends of each plate is about 6 mm, each plate also including a narrowed neck portion between said first and second ends to facilitate deformation of said plate during installation of said coil spring assembly.

33. The orthodontic coil spring assembly of claim 32, further comprising an expandable sheath for covering said coil spring.

* * * * *

UNITED STATES PATENT AND TRADEMARK OFFICE
CERTIFICATE OF CORRECTION

PATENT NO. : 5,545,037
DATED : August 13, 1996
INVENTOR(S) : Takeshi Watanabe

It is certified that error appears in the above-indentified patent and that said Letters Patent is hereby corrected as shown below:

On the cover page, item [19], should read --Watanabe--.

On the cover page, [75] Inventor should read:

--TAKESHI WATANABE--

Signed and Sealed this

Seventh Day of January, 1997

Attest:

BRUCE LEHMAN

Attesting Officer

Commissioner of Patents and Trademarks